(12) United States Patent
    Das

(10) Patent No.: US 9,705,277 B2
(45) Date of Patent: Jul. 11, 2017

(54) TECHNIQUE FOR THE DETECTION OF TRACE GASES USING INTRACAVITY FIBER LASER ABSORPTION SPECTROSCOPY (IFLAS)

(71) Applicant: Lakehead University, Thunder Bay (CA)

(72) Inventor: Gautam Das, Thunder Bay (CA)

(73) Assignee: LAKEHEAD UNIVERSITY, Thunder Bay, Ontario (CA)

( * ) Notice: Subject to any disclaimer, the term of this patent is extended or adjusted under 35 U.S.C. 154(b) by 0 days.

(21) Appl. No.: 15/158,124

(22) Filed: May 18, 2016

(65) Prior Publication Data

US 2017/0025812 A1    Jan. 26, 2017

Related U.S. Application Data

(60) Provisional application No. 62/164,203, filed on May 20, 2015.

(51) Int. Cl.
| | | |
|---|---|---|
| G01J 4/00 | (2006.01) |
| G01N 21/39 | (2006.01) |
| H01S 3/067 | (2006.01) |
| H01S 3/10 | (2006.01) |
| H01S 3/11 | (2006.01) |
| H01S 3/094 | (2006.01) |
| G01J 3/10 | (2006.01) |
| G01J 3/02 | (2006.01) |
| G01J 3/42 | (2006.01) |
| H01S 3/16 | (2006.01) |
| G01N 33/00 | (2006.01) |

(52) U.S. Cl.
    CPC ........ *H01S 3/06791* (2013.01); *G01J 3/0218* (2013.01); *G01J 3/0224* (2013.01); *G01J 3/10* (2013.01); *G01J 3/42* (2013.01); *G01N 21/39* (2013.01); *H01S 3/094088* (2013.01); *H01S 3/10061* (2013.01); *H01S 3/1115* (2013.01); *G01N 33/0037* (2013.01); *G01N 2021/396* (2013.01); *G01N 2201/06113* (2013.01); *G01N 2201/08* (2013.01); *H01S 3/0675* (2013.01); *H01S 3/06712* (2013.01); *H01S 3/1608* (2013.01)

(58) Field of Classification Search
    CPC .... G01J 4/00; G01J 3/10; G01N 21/39; H01S 3/06791
    USPC ......................................................... 356/364
    See application file for complete search history.

(56) References Cited

U.S. PATENT DOCUMENTS

2015/0102240 A1    4/2015  Zhu et al.
2016/0248217 A1*   8/2016  Fermann ............. H01S 3/06712

* cited by examiner

*Primary Examiner* — Roy M Punnoose
(74) *Attorney, Agent, or Firm* — Kyle R. Satterthwaite; Ryan W. Dupuis; Ade & Company Inc

(57) ABSTRACT

A gas detection system uses intracavity fiber laser absorption spectroscopy. The fiber laser is stabilized by a saturable absorber, and the sensitivity is enhanced by multiple circulations of amplified spontaneous emission light under threshold conditions, and multi-longitudinal mode oscillation of the laser.

5 Claims, 7 Drawing Sheets

FIG. 6
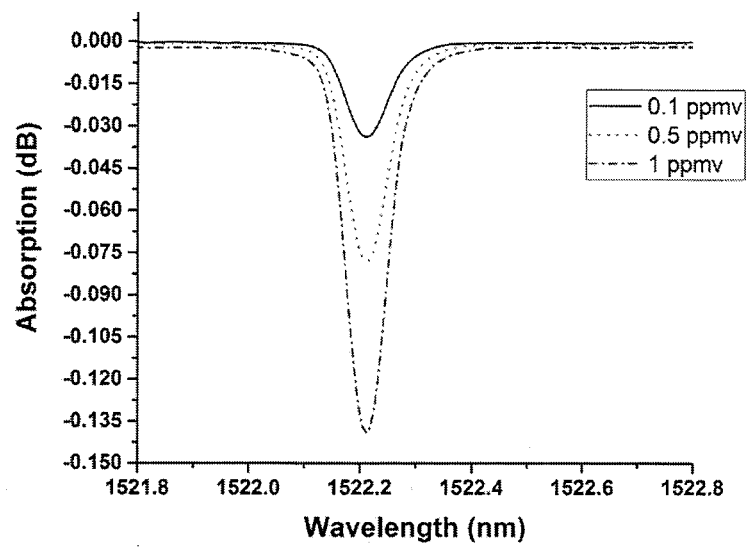
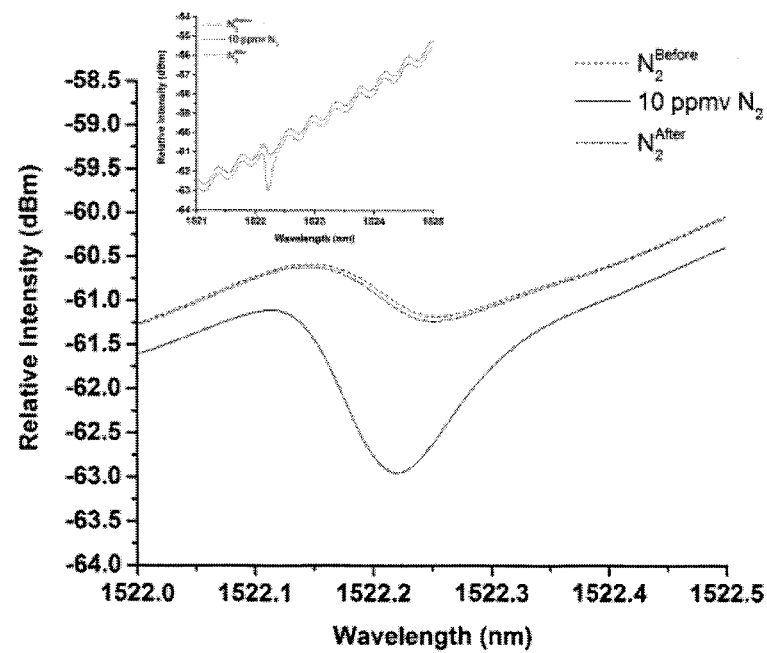
FIG. 6A

FIG. 6B
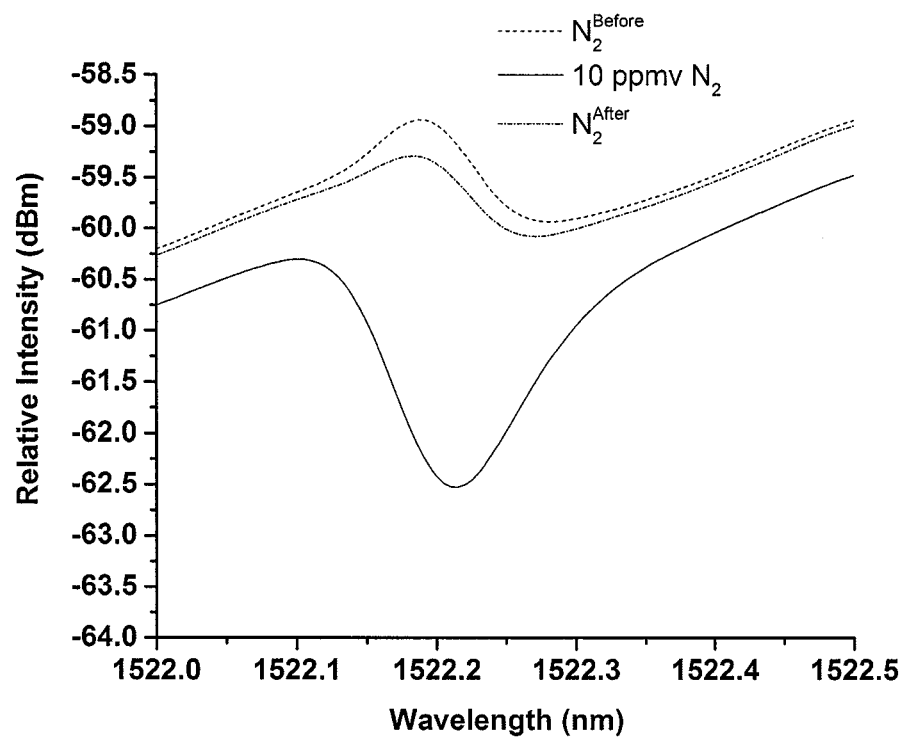
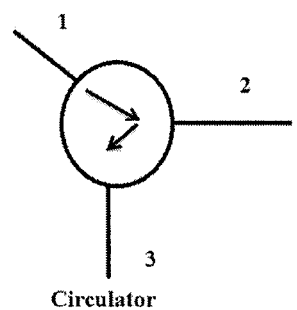
FIG. 7

FIG. 8A
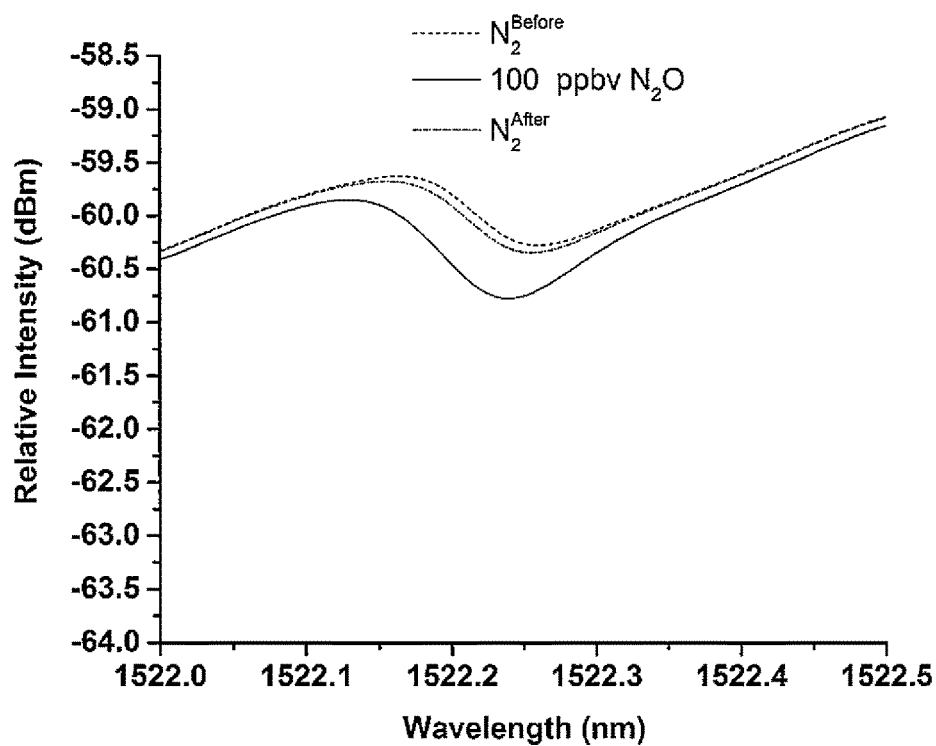
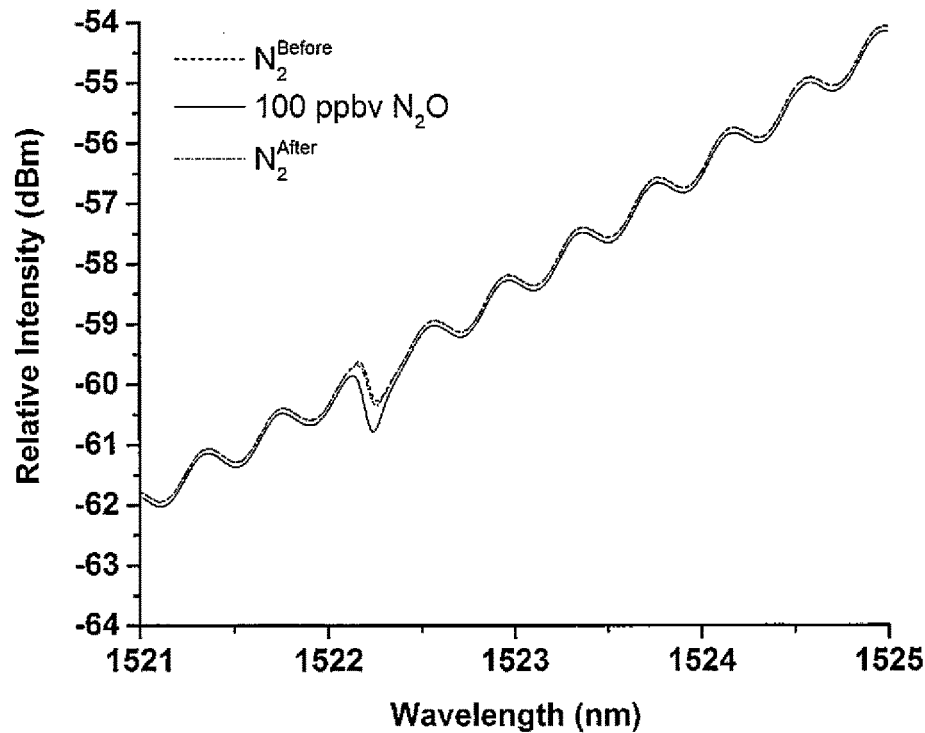
FIG. 8B

TECHNIQUE FOR THE DETECTION OF TRACE GASES USING INTRACAVITY FIBER LASER ABSORPTION SPECTROSCOPY (IFLAS)

FIELD OF THE INVENTION

The present invention relates generally to detection of gases using Intracavity Fiber Laser Absorption Spectroscopy, and more particularly to detection of trace gases using spectral analysis of amplified spontaneous emission (ASE) from a multi-longitudinal mode fiber ring cavity laser operating at threshold conditions.

BACKGROUND

Nitrous oxide ($N_2O$) gas is a minor constituent in the earth's atmosphere (~300 ppbv), but the levels of $N_2O$ are rising due to human augmentation of the nitrogen cycle. $N_2O$ contributes to the destruction of the stratospheric ozone layer, increases the greenhouse effect of the atmosphere, and has a direct impact on human health. As a greenhouse gas (GHG), it is ~300 times more destructive than carbon dioxide ($CO_2$). Agricultural fertilizers are major sources of $N_2O$. As the global population increases in the next few decades, the use of fertilizer will also increase to meet the demand for food.

The current technology used to quantify the emission of $N_2O$ from agricultural fields caused by fertilizer application is complex and very expensive. In most cases, it involves collecting emitted gases and analyzing them using GC or FTIR spectroscopy in the laboratory, or using very expensive laser spectroscopy methods including cryo-cooled Pb-salt tunable diode laser spectroscopy and cavity ring down spectroscopy. A highly sensitive technique to provide real-time analysis at ambient temperature is in demand. Further, $N_2O$ has weak absorption lines in the 1.55 μm wavelength band, which falls within the emission band of Erbium-doped fiber. So a real-time analyzer in the above band will not only be able to operate at room temperature but will can also be developed with available optical and electronic components used in the telecommunication industry, which will make the system compact and cost effective, and make it possible for the system to incorporate a multipoint sensor using fiber optic networking (see reference [1]).

A number of articles about $N_2O$ have identified the overtones of the characteristic absorption (fundamental) and the combinations of the overtones in the near infrared (NIR) region (1-2 μm) of the electromagnetic spectrum using Fourier transform absorption spectroscopy (see references [2-7]), cavity ring down spectroscopy (see references [8-10]) and intracavity laser absorption spectroscopy (see reference [11]).

U.S. Patent Application Publication No. 2015/0102240 discloses a gas detection system featuring an inner ring cavity fiber laser with a saturated absorption optical fiber. The system measures the laser intensity after passing through a gas cell situated in the closed-loop optical circuit of the ring cavity, and compares this against a previously stored reference value to detect changes in the concentration of a target gas found within the gas cell. While such techniques may be appropriate when the gas absorption or gas concentration is very high, the same solution is not suitable for detection of trace gases.

In the present application, Applicant presents for the first time a new technique based on intracavity fiber laser absorption spectroscopy (IFLAS), which can detect the weak absorption lines in the 1.52 μm band for $N_2O$ available from HITRAN (see reference [12]). The new technique uses the amplified spontaneous emission (ASE) present inside the laser cavity, and testing of a prototype has found the system capable of detecting and quantifying $N_2O$ gas at concentrations of around and below 100 ppbv [Reference 13].

SUMMARY OF THE INVENTION

According to one aspect of the invention, there is provided a gas detection system using intracavity fiber laser absorption spectroscopy, said system comprising:

a multi-longitudinal mode ring cavity fiber laser comprising:
  a closed-loop optical circuit in which a wavelength division multiplexer, a first active optical fiber, a first optical isolator, a variable optical attenuator, a gas cell, an optical circulator, a polarization controller, and a second optical isolator are connected successively;
  a fiber Bragg grating connected to the closed-loop optical circuit via the optical circulator;
  a second active optical fiber coupled between the fiber Bragg grating (FBG) and the optical circulator as a saturable absorber;
  a pump light source optically coupled to the closed-loop optical circuit by the wavelength division multiplexer so as to generate amplified spontaneous emission (ASE) in the first active optical fiber, of which forward-propagating ASE is transmitted onward from the first active optical fiber through the first optical isolator, the optical attenuator, the gas cell, the circulator and the second active optical fiber to the FBG, from which a first portion of the forward-propagating ASE is reflected back to the closed-loop optical circuit, via the second active optical fiber and the optical circulator, for use in generating a laser; and an optical spectrum analyzer optically coupled to the FBG to spectrally analyze a second portion of the forward-propagating ASE transmitted through the FBG;
  wherein the attenuator is set to establish and maintain a threshold condition of the laser and a flat spectrum of the forward-propagating ASE in vicinity to a lasing wavelength of laser, which is set by the FBG.

Preferably the first active optical fiber comprises a polarization-maintaining erbium-doped fiber.

Preferably the second active optical fiber comprises an unpumped polarization-maintaining erbium-doped fiber.

In one embodiment, a coupler is connected to the closed-loop optical circuit between the circulator and the polarization controller for monitoring an output of the laser;

According to a second aspect of the invention, there is provided a method of detecting a gas comprising:

generating amplified spontaneous emission (ASE) in a first active fiber of a multi-longitudinal mode ring cavity fiber laser;

guiding forward-propagating ASE from said first active fiber through a gas cell and onward through an optical circulator and a second active fiber to a fiber Bragg grating of the ring cavity, from which a portion of the forward-propagating ASE is reflected back through the second active fiber for use in generating a laser;

performing attenuation in the ring cavity to establish and maintain a threshold condition of the laser and a flat spectrum of the forward-propagating ASE in vicinity to a lasing wavelength of laser, which is set by the FBG;

spectrally analyzing a second portion of the forward-propagating ASE transmitted through the fiber Bragg grating to detect presence of a target gas in the gas cell.

BRIEF DESCRIPTION OF THE DRAWINGS

One embodiment of the invention will now be described in conjunction with the accompanying drawings in which:

FIG. 7 schematically illustrates an optical circulator of the system of FIG. 1.

FIG. 8A shows transmission spectra of the laser with reference gas $N_2$ and $N_2O$ gas for a pump current of 130.0 mA, with the full spectrum shown separately in FIG. 8B.

DETAILED DESCRIPTION

Figure 1:
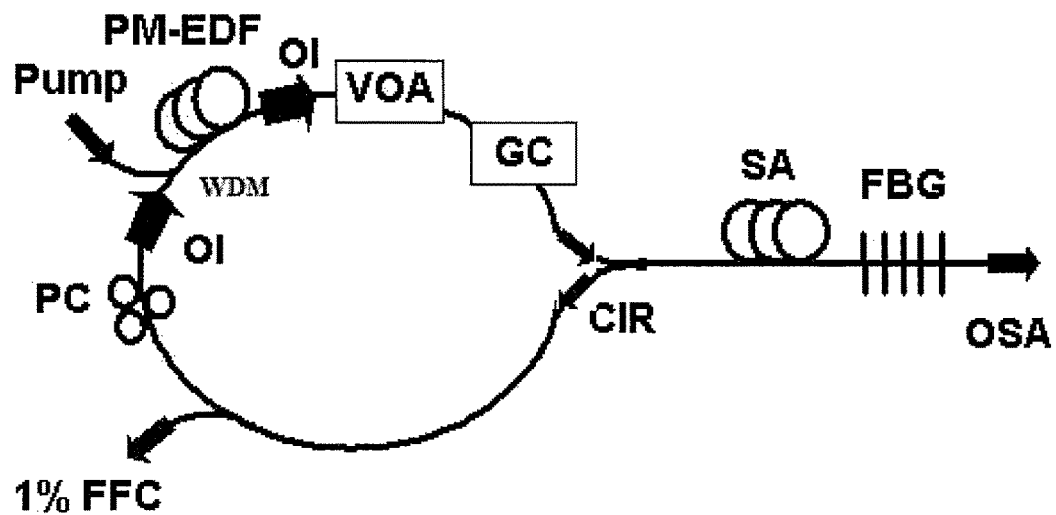
FIG. 1 is a schematic diagram of a fiber ring cavity laser gas detection system according to the present invention.

FIG. 1 schematically illustrates a gas detection system according to one embodiment of the present invention. The system is primarily comprised of a ring cavity fiber laser, which in a known manner features of a unidirectional closed-loop optical circuit with a first active fiber fed by a pump light source through a wavelength division multiplexer, and, outside the closed-loop circuit, a second active fiber coupled between an optical circulator of the closed-loop circuit and a fiber Bragg grating. In the illustrated embodiment of the present invention, a first optical isolator, an attenuator, and a gas cell are successively connected in series between the wavelength division multiplexer and the optical circulator. Continuing in this direction around the closed-loop circuit, a coupler, a polarization controller and a second optical isolator are successively connected in series between the circulator and the wavelength-division multiplexer.

In a prototype of the present invention, which served as an experimental setup used for the detection of $N_2O$, the first active fiber of the unidirectional ring cavity consists of a polarization-maintaining erbium-doped fiber (PM-EDF) with length, core dimension, absorption and Numerical Aperture (NA) of 5 m, 3.8×14.8 μm, 7.2 dB/m at 980 nm and 0.15, respectively; the attenuator is a variable attenuator (VOA) to adjust the total loss in the cavity in order to obtain the desired emission spectrum of PM-EDF; the gas cell is a multipass gas cell (Herriot cell) with an effective path length of 30 m and a volume of approximately 0.9 liter; the second active fiber is an unpumped PM-EDF of length 0.50 m that serves as the saturable absorber (SA); the fiber Bragg grating (FBG) has a reflectivity of 85.16%, a peak wavelength of approximately 1522.22 nm and a bandwidth of 0.168 nm, which was selected to match closely with the absorption peak of the $N_2O$ gas under investigation; the coupler is a 1% 2×2 fused fiber coupler (FFC) to monitor the power from the resonator using a power meter; and the polarization controller is an all-fiber polarization controller to control the polarization state of the light inside the cavity. Two polarization-independent optical isolators and a polarization-independent optical circulator guaranteed the unidirectional propagation of light inside the cavity, and an optical spectrum analyzer (OSA) of resolution 0.05 nm was used to collect the output of the system. The attenuator was connected by an angled connector. The 0.5 m length of the unpumped PM-EDF does not provide a line narrowing effect. The counter propagating light inside the cavity (i.e. the light flowing toward the FBG from the closed-loop circuit and the light being reflected back to the closed-loop circuit from the FBG) produce a transient grating which track the peak wavelength of the fiber Bragg grating.

In the prototype, standard single-mode fiber was used for portions of the ring cavity other than the PM-EDF fibers. However, it will be appreciated that in other embodiments of the present invention, multimode fiber (MMF) could also be used. The 2×2 coupler in the prototype was used to monitor the laser output for any fluctuation, and confirm that no light propagated in the reverse direction (counter-clockwise in FIG. 1). Other embodiments could alternatively replace the 2×2 coupler with 1×2 coupler, or omit the coupler altogether.

The presence of two isolators increases the stability of the cavity. The purpose of the two isolators is to obtain unidirectional flow of signal light through the polarisation-maintaining erbium-doped fiber (PM-EDF) that defines the gain medium of the laser cavity. The unidirectional flow of light eliminates any interference of light inside the gain medium and thus eliminates "Spatial Hole Burning effect". Attaching the optical isolator between the pump and the attenuator reduces any back-reflection from the attenuator port. The isolator between the polarization controller and the pump eliminates backward-propagating amplified spontaneous emission (ASE) from the PM-EDF, preventing it from reaching the FFC and the circulator. The polarization independent optical circulator stops any back-reflected light from entering the Saturable absorber (SA) and FBG sections. FIG. 7 shows such a circulator, in which the working principle is that light can go only in one direction, compared to a 2×2 coupler. So any input at port 1 will be transmitted to port 2 and any input at port 2 will be transmitted to port 3. It does not work in any other direction. The presence of this component in the cavity increased the stability of the laser system and measurement accuracy.

The all-fiber polarization controller is used to control the polarization state of the light inside the cavity. It is very important to obtain a very stable laser (or ASE) light in order to detect very small fluctuation of gas concentration or to detect very lower gas concentration. The use of Polarization-maintaining Erbium-doped fiber (PM-EDF) as the gain medium and saturable absorber (SA) gives the desired stability of the laser or cavity ASE, and the transient grating formed inside the saturable absorber. The polarization controller allows the excitation of erbium ions along a particular direction of polarization (the shape of the polarization-maintaining fiber is elliptic) and increases the stability of the system. With the presence of the polarization controller, a separate active stabilization scheme is not required for room temperature operation. By adjusting plates of the polarization controller, one can stabilize the laser line and reduce mode-hopping, in the multi-longitudinal mode laser cavity.

Figure 4:
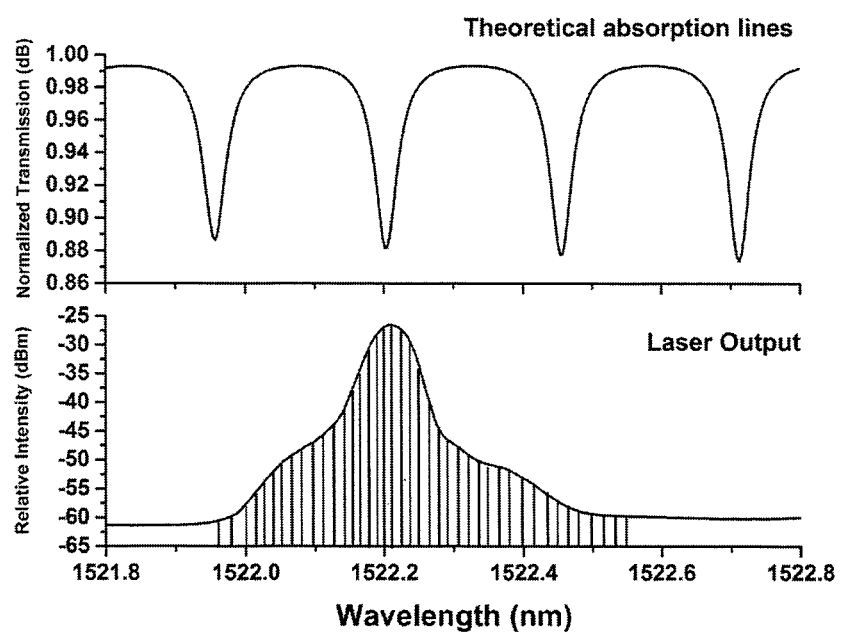
FIG. 4 shows output of the fiber ring cavity laser gas detection system obtained using an optical spectrum analyzer and theoretical absorption lines obtained using GATS Spectral Calculator (HITRAN 2012).

In the prototype, the total length of the laser cavity was approximately 50 m (approximately 20 m of fiber, including the gain fiber, plus the approximately 30 m effective path length of the gas cell), which corresponds to a longitudinal mode spacing of ~4 MHz. Thus the output of the laser (at wavelength ~1522.22 nm, as dictated by the peak wavelength of the FBG) contained many closely spaced longitudinal modes. In general a laser that contains multiple-longitudinal modes is susceptible to mode hopping due to environmental fluctuations such as temperature. The transient grating formed inside the SA, due to the counter-propagating light waves, acts as a tracking filter and stabilizes the laser by eliminating the mode hopping. The bandwidth of the transient grating is inversely proportional to the length of the SA; thus, by increasing the length of the SA a very narrow band transient grating can be obtained. The drawback is that the threshold pump power of the laser increases. Further, the use of a PM-EDF as the SA increases the stability of the transient grating. The transient grating and the FBG form a Fabry-Perot cavity. Further, the Fabry-Perot and the unidirectional ring cavity form an overlapping resonating cavity. The output of the laser was modulated by the Fabry-Perot cavity, which stabilizes the laser (see reference [14]). It was found that a multi-longitudinal mode laser provides very high sensitivity in IFLAS if the absorption linewidth is smaller than the laser linewidth (see references [15,16]). Further, reference 17 also shows an increase of absorption sensitivity by a factor of $10^5$ due to the presence of a number of oscillating longitudinal-modes. FIG. 4 shows the output of the IFLAS and theoretical absorption lines. The absorption peak of the gas superimposed with the longitudinal modes (a few of which are shown by vertical lines inside the laser line) of the laser and thus increased the sensitivity.

In the system of FIG. 1, amplified spontaneous emission (ASE) present inside the laser cavity is used as the source of light for the absorption spectroscopy on the contents of the gas cell. By placing the gas cell (GC) before the circulator, maximum ASE is allowed to be transmitted through the GC and thus maximum interaction of the ASE with the gas sample occurs. Further, the gas cell is located between the VOA (Variable optical attenuator) and the circulator. In general, the ASE spectrum from an erbium-doped fiber is not flat, which is desirable in the present case. The purpose of the attenuator is to adjust the loss in the cavity in order to obtain the desired emission spectrum of PM-EDF.

Figure 2A:
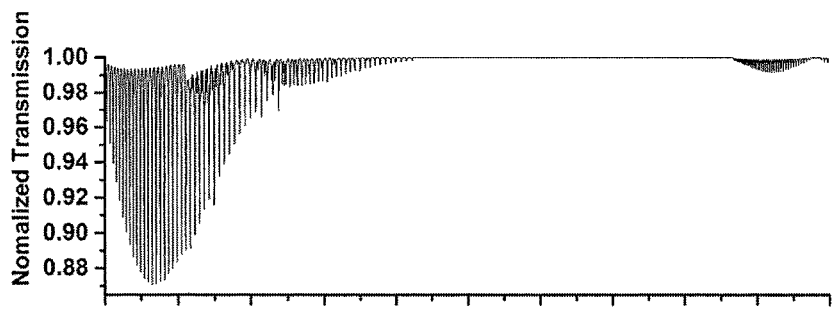
FIG. 2(a) shows theoretical absorption lines for 2% $N_2O$ and a gas cell path length of 30 m obtained using GATS Spectral Calculator (HITRAN 2012)
Figure 2B:
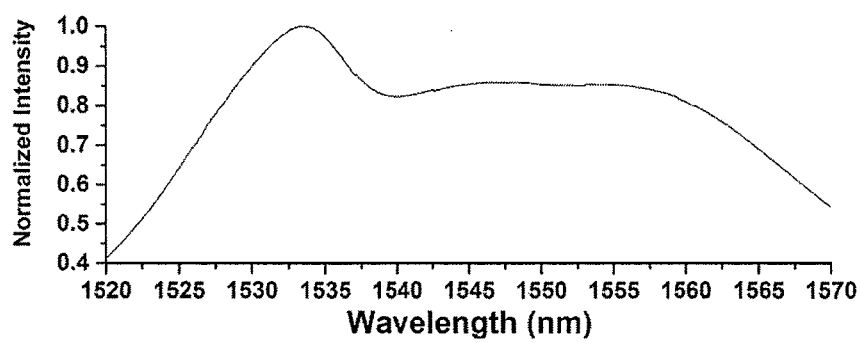
FIG. 2(b) shows ASE spectrum for PM-EDF.
Figure 3:
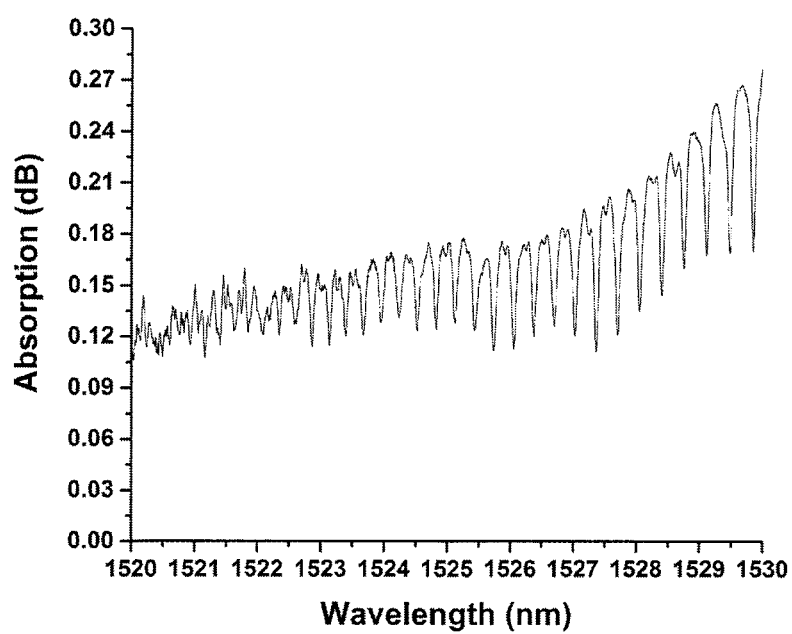
FIG. 3 shows absorption lines for 2% $N_2O$ after subtracting the reference gas $N_2$.

It is evident from FIG. 2 (a) that high absorption occurs at ~1522 nm. An experiment was performed following the prior art experimental configuration for intracavity absorption spectroscopy, which uses ASE light inside the cavity, as described in reference [18], with the gas cell of path length 30 m. The attenuator inside the ring cavity was used to obtain a flat ASE spectrum in the C and L band regions. The minimum concentration of the $N_2O$ gas the system could detect using the prior art techniques was 2% [FIG. 3]. Further, the technique reported in reference [18] was able to detect lower concentration for gases (e.g. C2H2 and CO2) that have higher absorption in the C band (~1534 nm) region than $N_2O$. As shown in FIG. 2(a) the maximum absorption for $N_2O$ is around 1522 nm. In order to use the procedure described in reference [18] a flat ASE spectrum was required, but it was difficult to take advantage of the ASE light available in the cavity to detect $N_2O$, because the intensity of the ASE spectrum in the 1522 nm band was much lower than that in the C and L band region (FIG. 2(b)). Further, it was not flat, which is one of the requirements for the implementation of the method.

The experimental setup illustrated in FIG. 1 and described in further detail above eliminated the problem described in the preceding paragraph and allowed detection of $N_2O$ at a lower concentration (100 ppbv). In the technique in accordance with the present invention, the laser wavelength, which was selected by the FBG, was kept at the threshold position, so that the ASE spectrum close to the laser wavelength was almost flat (in other words, also close to the threshold). Thus, the ASE light inside the cavity circulated multiple times and enhanced the effective path length of the cavity. In turn, the sensitivity of detection was also enhanced due to the large absorption path length provided by the 30 m effective path length of the multi-pass gas cell. While the effective path length may be varied, a minimum path length of 25 m is employed in embodiments using a multipass gas cell. In alternative embodiments, the gas cell may take the form of a Photonics Crystal Fiber (hollow core fiber), which may have a shorter length, for example 20 m, and therefore may allow a smaller hand-held configuration of the system.

Figure 5:
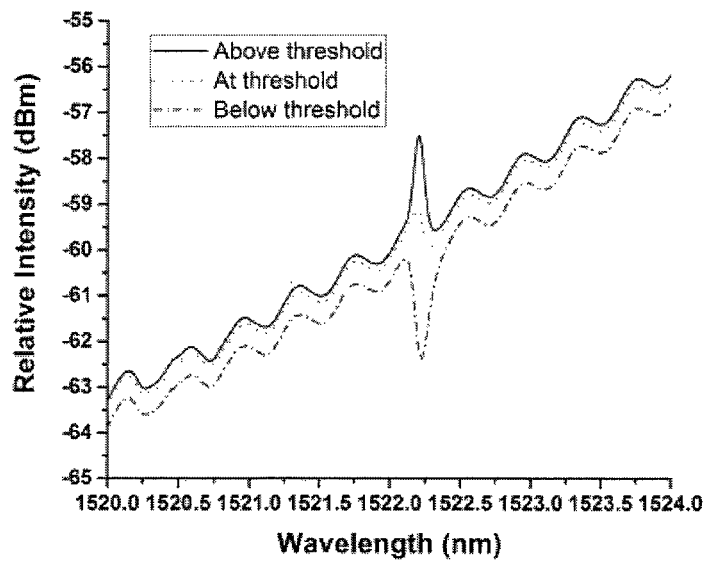
FIG. 5 shows output intensity of the laser (λ=1522.22 nm) of the system at different attenuations with $N_2$ gas inside the gas cell.
Figure 6C:
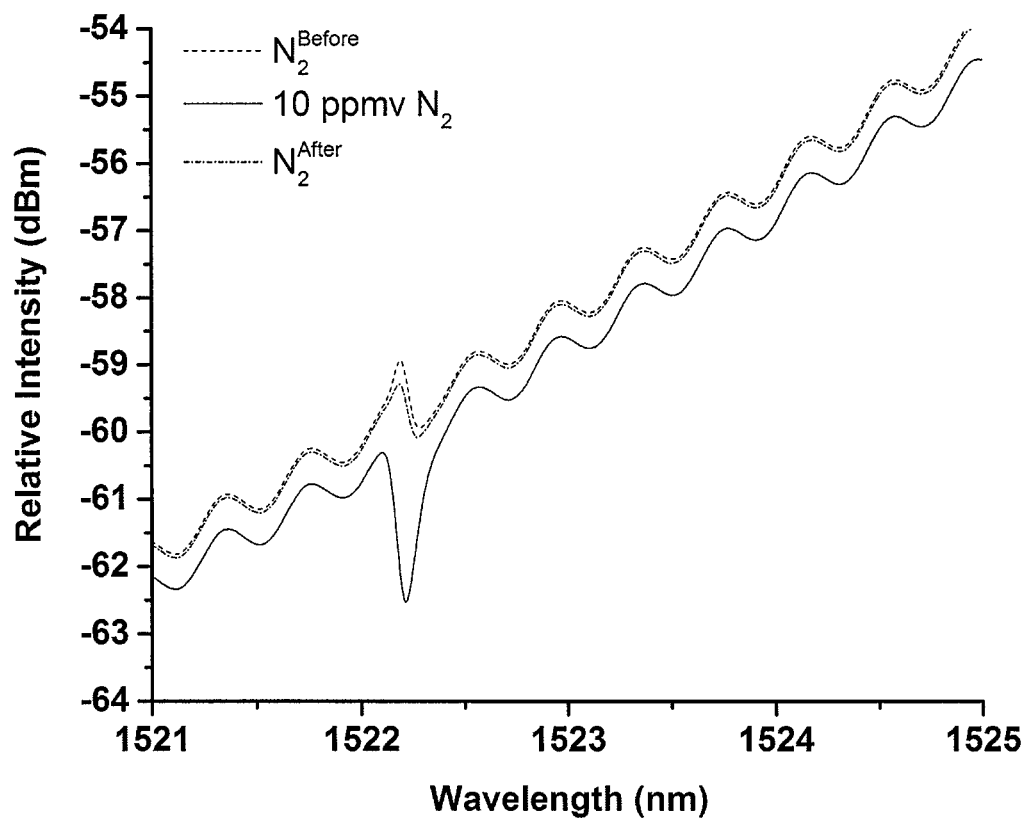
FIG. 6 shows absorption spectrum of $N_2O$ gas at different concentrations after subtracting the $N_2$ gas spectrum as background.
FIG. 6A shows transmission spectra of the laser with reference gas $N_2$ and $N_2O$ for a pump current of 99 mA, with the full spectrum shown in the inset graph.
FIG. 6B shows transmission spectra of the laser with reference gas $N_2$ and $N_2O$ for a pump current of 130 mA, with the full spectrum shown separately in FIG. 6C.

FIG. 5 shows the output of the laser obtained using the OSA. The attenuation of the cavity was adjusted using the VOA in order to obtain the condition such that the laser is at threshold. Further, the regions close to laser wavelength were also close to the threshold value, so any small change in the cavity loss changed the output of the laser. In other words, the cavity becomes very sensitive to changes in loss due to absorption by the gas molecule inside the laser cavity. It is also shown in FIG. 4 that the absorption line of $N_2O$ around 1522.22 nm superimposed with many longitudinal modes inside the laser line, because the separation between two modes was approximately 4 MHz. A number of longitudinal-modes will disappear once they coincide with the absorption line. As the erbium-doped fiber is a homogeneous gain medium at room temperature, any small loss in the cavity will change the cavity resonance condition [e.g. due to longitudinal-mode competition the laser peak, determined by the FBG peak reflection, can be shifted slightly either to a longer or shorter wavelength or can disappear completely depending on the concentration of gas and location of the laser peak]. The output showed a very large dip at higher concentrations of the gas molecules, similar to that shown in FIG. 5, which was obtained by adjusting the attenuation of the cavity using VOA. It is to be noted that the above threshold condition can be achieved by adjusting the pump current of the laser at constant attenuation. The attenuator also helped make the erbium ASE spectrum lower in the C band (~1530 nm) so that no lasing line appeared in that region, and thus obtained a much flatter spectrum in the desired spectral region in the 1522 nm band. The interference pattern visible in FIG. 5, and in the inset of FIGS. 6A, 6B and 8, is due to the etalon effect between the connector and quartz windows in the gas cell. This pattern was found to disappear once the spectrum with the gas sample was subtracted from the reference spectrum (for $N_2$ gas).

In order to obtain the absorption spectrum from the system, a reference spectrum was obtained after filling the cell with 100% $N_2$ gas, and then a spectrum for each concentration of $N_2O$ was obtained. The cell was flushed with $N_2$ after the scanning for each concentration was completed. FIG. 6 shows the absorption spectrum when the background spectrum (for $N_2$) was subtracted. The system was able to detect 100 ppbv. FIGS. 6A and 6B show the transmission spectra of the system with the reference gas $N_2$ (Praxair, Canada, Research Grade, Nitrogen 6.0) and $N_2O$ (Praxair, Canada, certified concentration of $N_2O$: 9.95 ppm+ $N_2$ balance) gas for two different pump currents (Ip), specifically 99 mA and 130 mA, respectively. The gas cell was flushed with $N_2$ before and after the scanning with the 10 ppm $N_2O$ gas inside the gas cell. The transmission spectra are given as $N_2^{Before}$ and $N_2^{After}$ respectively. One can obtain the absorption spectrum by subtracting the $N_2O$ spectrum from the average of the $N_2$ spectra. As evident from the figures, the high enhancement was obtained when the laser was operating close to threshold condition ($I_p$=130 mA).

In order to study the sensitivity of the system, $N_2O$ gas was prepared at lower concentrations from certified standard mixtures (PRA)(IAR, Canada). A mass flow controller (OMEGA, model: FMA 5412) controlled by LABVIEW was used to prepare a 6 L gas mixture with $N_2O$ and $N_2$ (PRAXIAR, Canada, Research grade, Nitrogen 6.0) in a 10 L Tedlar sampling bag (Cole-Parmer Canada). For example, to achieve a concentration of 100 ppbv, 0.06 L of the 10 ppmv $N_2O$ (certified concentration: 9.95 ppmv+$N_2$ balance) @ 0.1 L/min for 36 seconds, and 5.94 L $N_2$ (Research Grade, Nitrogen 6.0) @ 0.5 L/min for 11 minutes 53 seconds were mixed. Similarly to make a 2% sample, use was made of 10% $N_2O$ (certified concentration: 10.1% +$N_2$ balance) and $N_2$.

For measurements of very low concentrations the polarization controller plates were adjusted carefully to obtain a stable laser line and pump current was adjusted to the threshold condition, so that the ASE close to the lasing wavelength became very sensitive to changes in loss from $N_2O$ gas absorption lines in this region. FIG. 8 shows the transmission spectra of reference gas $N_2$ and $N_2O$ gas of concentration 100 ppbv. The gas mixture was prepared using the method described in the above paragraph. The measured concentration using Gas Chromatography was ~127 ppbv. Thus it was concluded that the proposed system is capable of detecting $N_2O$ gas at ppbv concentration levels.

It was shown in Reference 18, one can obtain very large path length enhancement by minimizing the difference ($\delta$) between the cavity loss and the total gain of the erbium doped fiber, or by operating the laser close to the threshold. The presence of the FBG and saturable absorber inside the cavity [FIG. 1] made the laser highly stable, and thus a very low value for $\delta$ was achieved. The path length enhancement factor obtained was ~8200, when the laser was operating close to threshold conditions at $I_p$=130 mA. Thus the effective absorption path length of the cavity became ~246 km [8200 times of 30 m for the multipass gas cell], once the laser was operating under or close to threshold conditions.

In summary, a novel technique to detect gases at lower concentrations is presented herein above. The prototype of the system can detect a minimum concentration of 100 ppbv $N_2O$ gas. Because the cavity supports many longitudinal modes, it is not necessary to get a FBG whose peak wavelength matches perfectly with the absorption peak, which is a significant advantage of this process. Further, one can select different absorption lines using a tunable grating. Also, the use of FBG allows operation in the shorter wavelength region of the ASE spectrum. The SA present inside the cavity eliminates mode hopping. For operation at temperatures other than room temperature, the FBG can be placed at constant temperature to eliminate any fluctuation of peak wavelengths due to high temperature changes; it is also possible to add an active FBG stabilization scheme found in reference [19], the entirety of which is incorporated herein by reference.

While described above in the context of $N_2O$ detection, other gases can also be detected with the system of the present invention, examples of which may include $C_2H_2$, $CH_4$, and $H_2S$, which is an important biomarker for concussions. Since various modifications can be made in my invention as herein above described, and many apparently widely different embodiments of same made within the scope of the claims without departure from such scope, it is intended that all matter contained in the accompanying specification shall be interpreted as illustrative only and not in a limiting sense.

REFERENCES

Each Incorporated Herein by Reference in Entirety

1. G. Whitenett, G. Stewart, H. B. Yu, and B. N. Culshaw, "Investigation of a tuneable mode-locked fiber laser for application to multipoint gas spectroscopy," Journal of Lightwave Technology 22, 813 (2004).
2. A. Campargue, D. Permogorov, M. Bach, M. A. Temsamani, J. V. Auwera, M. Herman, and M. Fujii, "Overtone Spectroscopy in Nitrous-Oxide," Journal of Chemical Physics 103, 5931 (1995).
3. L. Wang, V. I. Perevalov, S. A. Tashkun, B. Gao, L. Y. Hao, and S. M. Hu, "Fourier transform spectroscopy of $N_2O$ weak overtone transitions in the 1-2 mu m region," Journal of Molecular Spectroscopy 237, 129 (2006).
4. B. Gao, C. Y. Wang, Y. Lu, A. W. Liu, and S. M. Hu, "High-resolution infrared spectroscopy of N-15(2) O-16 in the 3500-9000 cm(-1) region," Journal of Molecular Spectroscopy 259, 20 (2010).
5. K. F. Song, A. W. Liu, H. Y. Ni, and S. M. Hu, "Fourier-trans form spectroscopy of (NNO)—N-15-N-14-O-16 in the 3500-9000 cm(-1) region," Journal of Molecular Spectroscopy 255, 24 (2009).
6. H. Y. Ni, K. F. Song, V. I. Perevalov, S. A. Tashkun, A. W. Liu, L. Wang, and S. M. Hu, "Fourier-transform spectroscopy of (NNO)—N-14N-15-O-16 in the 3800-9000 cm(-1) region and global modeling of its absorption spectrum," Journal of Molecular Spectroscopy 248, 41 (2008).
7. R. A. Toth, "Line positions and strengths of N2O between 3515 and 7800 cm(-1)," Journal of Molecular Spectroscopy 197, 158 (1999).
8. A. W. Liu, S. Kassi, P. Malara, D. Romanini, V. I. Perevalov, S. A. Tashkun, S. M. Hu, and A. Campargue, "High sensitivity CW-cavity ring down spectroscopy of N2O near 1.5 mu m (I)," Journal of Molecular Spectroscopy 244, 33 (2007).
9. A. W. Liu, S. Kassi, V. I. Perevalov, S. A. Tashkun, and A. Campargue, "High sensitivity CW-cavity ring down spectroscopy of N2O near 1.5 mu m (II)," Journal of Molecular Spectroscopy 244, 48 (2007).
10. A. M. Parkes, A. R. Linsley, and A. J. Orr-Ewing, "Absorption cross-sections and pressure broadening of rotational lines in the 3 nu(3) band of N2O determined by diode laser cavity ring-down spectroscopy," Chemical Physics Letters 377, 439 (2003).
11. E. Bertseva, A. Campargue, V. I. Perevalov, and S. A. Tashkun, "New observations of weak overtone transitions of N2O by ICLAS-VeCSEL near 1.07 mu m," Journal of Molecular Spectroscopy 226, 196 (2004).
12. L. S. Rothman, I. E. Gordon, Y. Babikov, A. Barbe, D. C. Benner, P. F. Bernath, M. Birk, L. Bizzocchi, V. Boudon, L. R. Brown, A. Campargue, K. Chance, E. A. Cohen, L. H. Coudert, V. M. Devi, B. J. Drouin, A. Fayt, J. M. Flaud, R. R. Gamache, J. J. Harrison, J. M. Hartmann, C. Hill, J. T. Hodges, D. Jacquemart, A. Jolly, J. Lamouroux, R. J. Le Roy, G. Li, D. A. Long, O. M. Lyulin, C. J. Mackie, S. T. Massie, S. Mikhailenko, H. S. P. Muller, O. V. Naumenko, A. V. Nikitin, J. Orphal, V. Perevalov, A. Perrin, E. R. Polovtseva, C. Richard, M. A. H. Smith, E. Starikova, K. Sung, S. Tashkun, J. Tennyson, G. C. Toon, V. G. Tyuterev, and G. Wagner, "The HITRAN2012 molecular spectroscopic database," Journal of Quantitative Spectroscopy & Radiative Transfer 130, 4(2013).
13. J. K. Valiunas, G. Stewart, and G. Das, "Detection of Nitrous Oxide (N2O) at Sub-ppmv Using Intracavity Absorption Spectroscopy," EIII Photonics Technology Letters, 28, 3(2016).
14. Z. J. Chaboyer, P. J. Moore, and G. Das, "Medium power single-mode single-wavelength fiber laser," Optics Commun. 282, 3100 (2009).
15. V. M. Baev, Latz T., and Toschek P. E., "Laser Intracavity absorption spectroscopy," Applied Physics B 69, 171 (1999).
16. R. Bohm, A. Stephani, V. M. Baev, and P. E. Toschek, "Intracavity Absorption-Spectroscopy with A Nd3+-Doped Fiber Laser," Optics Letters 18, 1955 (1993).
17. T. Hansch, A. L. Schawlow, and P. Toschek, IEEE Journal of Quantum Electronics, 8, 802 (1972).
18. N. Arsad, M. Li, G. Stewart, and W. Johnstone, "Intra-Cavity Spectroscopy Using Amplified Spontaneous Emission in Fiber Lasers," Journal of Lightwave Technology 29, 782 (2011).
19. Arsad N. and Stewart G., "Stable, tunable, and single-mode operation of an erbium-doped fibre laser system using a saturable absorber for gas spectroscopy applications," 2009), pp. 719525-719525-10.

The invention claimed is:

1. A gas detection system using intracavity fiber laser absorption spectroscopy, said system comprising:
a multi-longitudinal mode ring cavity fiber laser comprising:
  a closed-loop optical circuit in which a wavelength division multiplexer, a first active optical fiber, a first optical isolator, a variable optical attenuator, a gas cell, an optical circulator, a polarization controller, and a second optical isolator are connected successively;
  a fiber Bragg grating connected to the closed-loop optical circuit via the optical circulator;
  a second active optical fiber coupled between the fiber Bragg grating (FBG) and the optical circulator as a saturable absorber;
  a pump light source optically coupled to the closed-loop optical circuit by the wavelength division multiplexer so as to generate amplified spontaneous emission (ASE) in the first active optical fiber, of which forward-propagating ASE is transmitted onward from the first active optical fiber through the first optical isolator, the optical attenuator, the gas cell, the circulator and the second active optical fiber to the FBG, from which a first portion of the forward-propagating ASE is reflected back to the closed-loop optical circuit, via the second active optical fiber and the optical circulator, for use in generating a laser; and
an optical spectrum analyzer optically coupled to the FBG to spectrally analyze a second portion of the forward-propagating ASE transmitted through the FBG;
wherein the attenuator is set to establish and maintain a threshold condition of the laser and a flat spectrum of the forward-propagating ASE in vicinity to a lasing wavelength of laser, which is set by the FBG.

2. The system of claim 1 wherein the first active optical fiber comprises a polarization-maintaining erbium-doped fiber.

3. The system of claim 1 wherein the second active optical fiber comprises an unpumped polarization-maintaining erbium-doped fiber.

4. The system of claim 1 further comprising a coupler connected to the closed-loop optical circuit between the circulator and the polarization controller for monitoring an output of the laser.

5. A method of detecting a gas comprising:
generating amplified spontaneous emission (ASE) in a first active fiber of a multi-longitudinal mode ring cavity fiber laser;
guiding forward-propagating ASE from said first active fiber through a gas cell and onward through an optical circulator and a second active fiber to a fiber Bragg grating of the ring cavity, from which a portion of the forward-propagating ASE is reflected back through the second active fiber for use in generating a laser;
performing attenuation in the ring cavity to establish and maintain a threshold condition of the laser and a flat spectrum of the forward-propagating ASE in vicinity to a lasing wavelength of laser, which is set by the FBG,
spectrally analyzing a second portion of the forward-propagating ASE transmitted through the fiber Bragg grating to detect presence of a target gas in the gas cell.

* * * * *